United States Patent
Leysieffer et al.

[11] Patent Number: 6,131,581
[45] Date of Patent: Oct. 17, 2000

[54] PROCESS AND DEVICE FOR SUPPLY OF AN AT LEAST PARTIALLY IMPLANTED ACTIVE DEVICE WITH ELECTRIC POWER

[75] Inventors: Hans Leysieffer, Taufkirchen; Gerd M. Müller, Unterschleissheim, both of Germany

[73] Assignee: Dr.-ing. Hans Leysieffer, Taufkirchen, Germany

[21] Appl. No.: 09/332,605

[22] Filed: Jun. 14, 1999

[30] Foreign Application Priority Data

Jun. 23, 1998 [DE] Germany ............................ 198 27 898

[51] Int. Cl.⁷ ..................................................... A61B 19/00
[52] U.S. Cl. .................................. 128/899; 600/25; 607/35
[58] Field of Search ............................... 128/899; 600/25; 607/33, 34, 35, 1

[56] References Cited

U.S. PATENT DOCUMENTS

| | | |
|---|---|---|
| 3,861,397 | 1/1975 | Rao et al. . |
| 4,095,998 | 6/1978 | Hanson . |
| 4,134,408 | 1/1979 | Brownlee et al. . |
| 5,277,694 | 1/1994 | Leysieffer et al. . |
| 5,279,292 | 1/1994 | Baumann et al. . |
| 5,356,485 | 10/1994 | Kreider . |
| 5,411,467 | 5/1995 | Hortmann et al. . |
| 5,430,322 | 7/1995 | Koyanagi et al. . |
| 5,439,528 | 8/1995 | Miller . |
| 5,747,728 | 5/1998 | Fleurial et al. . |

FOREIGN PATENT DOCUMENTS

| | | |
|---|---|---|
| 0 076 070 | 4/1983 | European Pat. Off. . |
| 0 124 930 | 11/1984 | European Pat. Off. . |
| 0 341 902 | 11/1989 | European Pat. Off. . |
| 0 731 513 | 9/1996 | European Pat. Off. . |
| 0 761 256 | 3/1997 | European Pat. Off. . |
| 20 20 380 | 11/1970 | Germany . |
| 17 64 622 | 9/1971 | Germany . |
| 24 15 385 | 10/1975 | Germany . |
| 27 29 223 | 1/1979 | Germany . |
| 195 30 382 | 2/1997 | Germany . |
| 9-92889 | 4/1997 | Japan . |
| WO 94/14200 | 6/1994 | WIPO . |
| WO 94/16464 | 7/1994 | WIPO . |
| WO 95/04377 | 2/1995 | WIPO . |
| WO 96/15412 | 5/1996 | WIPO . |
| WO 97/44993 | 11/1997 | WIPO . |

OTHER PUBLICATIONS

H.–J. Wanjura, Future Power Supply of Cardiac Pacemakers in Midizinal–Markt/Acta Medicotechnica, 1969, No. 3, pp. 98–100.

*Primary Examiner*—Max Hindenburg
*Assistant Examiner*—Brian Szmal
*Attorney, Agent, or Firm*—Nixon Peabody LLP; David S. Safran

[57] ABSTRACT

An improved implantable thermoelectric energy converter for converting thermal energy generated by an implant wearer into electrical power for supplying electric power to an at least partially implanted active device, the implantable thermoelectric energy converter including a hot pole, a cold pole, and a plurality of individual modules electrically coupled to one another disposed between the hot pole and the cold pole. In particular, the hot pole thermally couples one end of the plurality of individual modules to an implantation site having a temperature substantially that of a core body temperature and the cold pole thermally couples another end of the plurality of individual modules to an implantation site closer to an outer skin surface of the implant wearer. In another embodiment, the implantable thermoelectric energy converter may also include an implantable energy storage for collecting and temporarily storing the electric power generated. In accordance with still another embodiment of the present invention, the cold pole of the implantable thermoelectric energy converter may form a cooling body having an enlarged surface area which is adapted to be positioned directly under a skin surface of the implant wearer. In yet another embodiment, the implantable thermoelectric energy converter may be implanted in the skull or neck area of the implant wearer's body.

32 Claims, 5 Drawing Sheets

PROCESS AND DEVICE FOR SUPPLY OF AN AT LEAST PARTIALLY IMPLANTED ACTIVE DEVICE WITH ELECTRIC POWER

BACKGROUND OF THE INVENTION

1. Field of the Invention

The invention relates to a process and a device for suppling electric power to an at least partially implanted active device such as a hearing device. More specifically, the present invention relates to such a process and a device where the electric power is produced by an implanted thermoelectric power converter based on the Seebeck effect.

2. Description of the Related Art

One process and a corresponding device where the electric power is produced by an implanted thermoelectric power converter based on the Seebeck effect have already been proposed generally by H.-J. Wanjura in the article *Future Power Supply of Cardiac Pacemakers* in Medizinal-Markt/Acta Medicotechnica, 1969, No. 3, pp. 98–100. One specific embodiment is shown in the German reference DE 195 30 382 A1. In that reference, the human body is used as a heat source for an energy converter which preferably consists of a zinc wire and a copper wire. The connection site of the two wires is exposed to a heat source which is preferably the human skin. Irregular voltage generated by the energy converter is then stored by a capacitor. The voltage which has been generated and stored can be sent to a microprocessor which can provide a constant DC voltage.

The use of the Seebeck effect to make available the electric power needed to operate an at least partially implantable active systems such as a hearing device has remained relatively unknown in medical practice. This could be attributed to the fact that the energy values which can be generated with the known devices is insufficient to provide adequate electrical power needed to operate such a device, especially since the temperature difference available to the thermoelectric energy converter is very small when the energy converter is implanted.

Therefore, there exists an unfulfilled need for a process and a device for providing electric power using an implanted thermoelectric converter based on the Seebeck effect. There also exists an unfulfilled need for such a process and a device which will provide adequate electrical power needed to operate an at least partially implantable active systems such as a hearing device despite the very small temperature difference.

SUMMARY OF THE INVENTION

The primary object of the present invention is to provide a process which can be used in medical practice as well as a corresponding device for providing electric power using an implanted thermoelectric converter based on the Seebeck effect.

Another important object of the present invention is to provide such a process and a device which will supply adequate electrical power to operate a partially or fully implanted active device such as a hearing device.

In accordance with one embodiment of the present invention, these objects are achieved by providing an improved implantable thermoelectric energy converter for converting thermal energy generated by an implant wearer into electrical power for supplying electric power to an at least partially implanted active device, the implantable thermoelectric energy converter including a hot pole, a cold pole, and a plurality of individual modules electrically coupled to one another disposed between the hot pole and the cold pole. In particular, the hot pole thermally couples one end of the plurality of individual modules to an implantation site having a temperature substantially that of a core body temperature and the cold pole thermally couples another end of the plurality of individual modules to an implantation site closer to an outer skin surface of the implant wearer. In another embodiment, the implantable thermoelectric energy converter may also include an implantable energy storage for collecting and temporarily storing the electric power generated. In accordance with still another embodiment of the present invention, the cold pole of the implantable thermoelectric energy converter may form a cooling body having an enlarged surface area which is adapted to be positioned directly under a skin surface of the implant wearer. In yet another embodiment, the implantable thermoelectric energy converter may be implanted in the skull or neck area of the implant wearer's body.

These and other objects, features and advantages of the present invention will become more apparent form the following detailed description of the preferred embodiments of the invention when viewed in conjunction with the accompanying drawings.

DETAILED DESCRIPTION OF THE INVENTION

The Seebeck effect-based thermoelectric energy converter 10 in accordance with one embodiment of the present invention is generally illustrated in FIGS. 1 to 4 and acts to directly convert the thermal energy of the body which is always available, into electrical energy so as to provide the active implant 26 with electrical energy. This is attained by effectively harnessing the temperature difference between the core temperature of the body and the surface temperature of the body in the implantation site. This temperature difference, as a thermodynamic form of energy, is converted directly into electrical energy by the Seebeck effect. The Seebeck effect is achieved, for example, by the structural pairing of different metals which are spaced far apart in thermoelectric series. Even more efficient use of the Seebeck effect may be attained by the constructive connection of specially doped semiconductor materials as discussed further below.

As will be evident from the discussion below, the thermoelectric energy converter 10 in accordance with the present invention provides major advantages over prior art electrical power supplying systems such as primary or secondary electrochemical elements U.S. Pat. No. 5,279,292 U.S. Pat. No. 4 134 408, EP 0 341 902 A), biofuel cells U.S. Pat. No. 3,861,397 and DE-OS 2,415,385), nuclear batteries (EP 0 761 256 A) and devices for direct conversion of the mechanical energy of motion into electric power by means of mechano-electrical converter principles (for example, of the cardiac muscle using piezoeffect) (DE-OS 2 729 223), mechanical microvariation systems and the like (DE 1 764 622 C, DE 2 020 380 C). These advantages include the fact that in the thermoelectric energy converter 10:

the Seebeck element does not work by self consumption, i.e. no substances are converted;

the Seebeck element has no mechanically moving parts and therefore is not subject to mechanical wear;

for the aforementioned reasons the service life is theoretically unlimited;

the implant wearer need not be concerned for the power supply of his implant for a long time;

power supply is largely constant on the input side since the temperature is regulated by the body.

Figure 1:
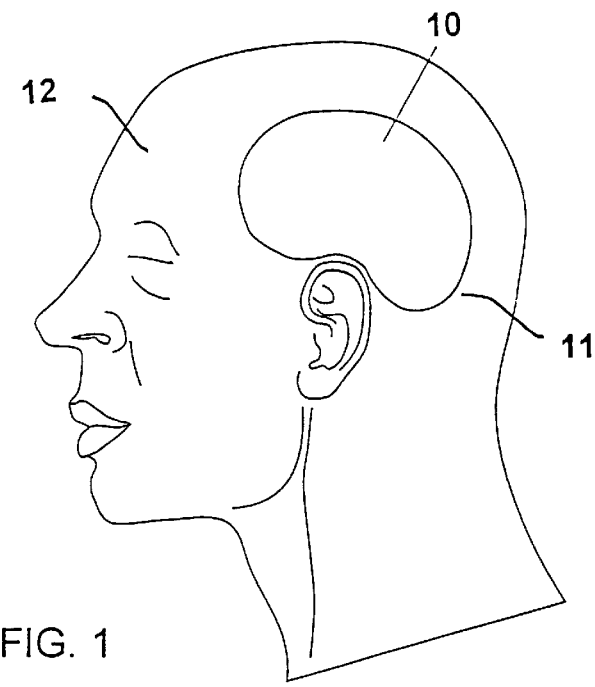
FIG. 1 shows a side view of a patient's head with a Seebeck effect-based thermoelectric energy converter in accordance with one embodiment of the present invention implanted under the skin in the mastoid area.
Figure 2:
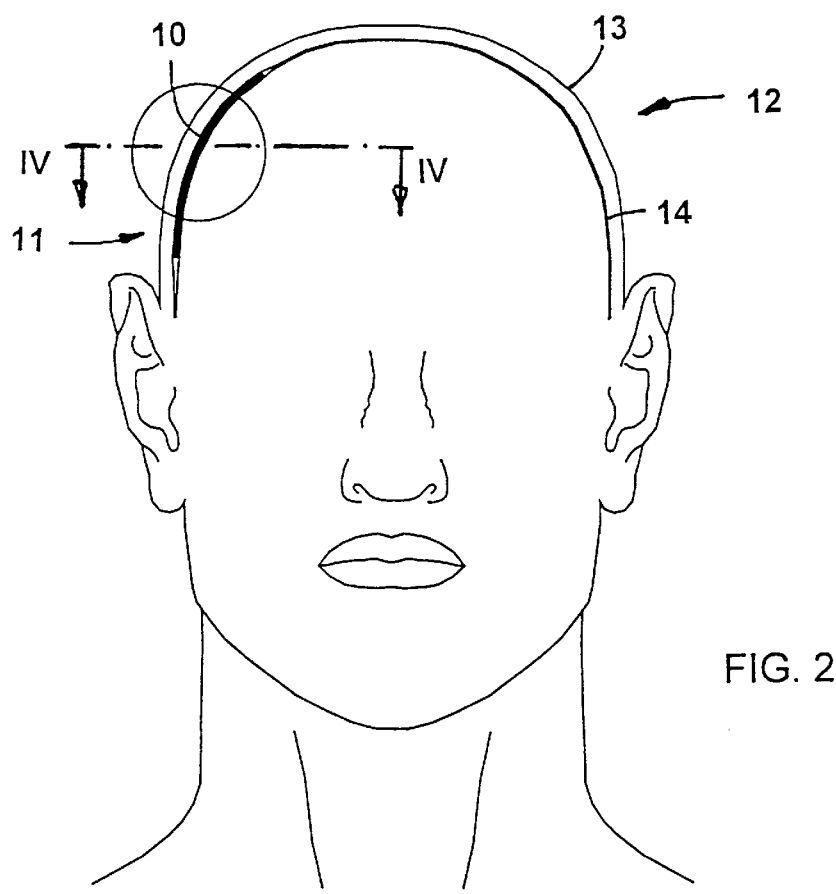
FIG. 2 is a partial cutaway front view of the thermoelectric energy converter of FIG. 1.
Figure 3:
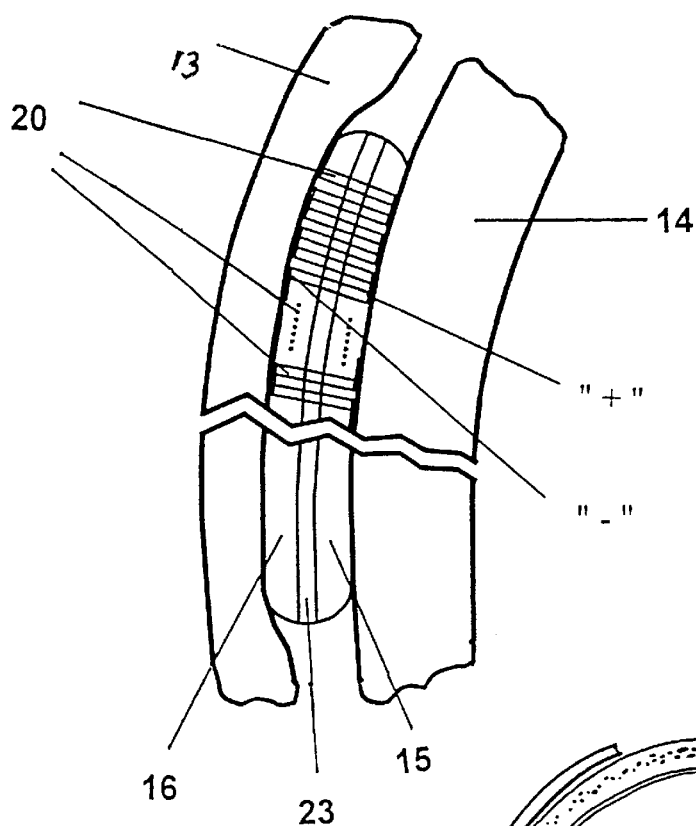
FIG. 3 is an enlarged partial cutaway view of the thermoelectric energy converter of FIG. 2.
Figure 4:
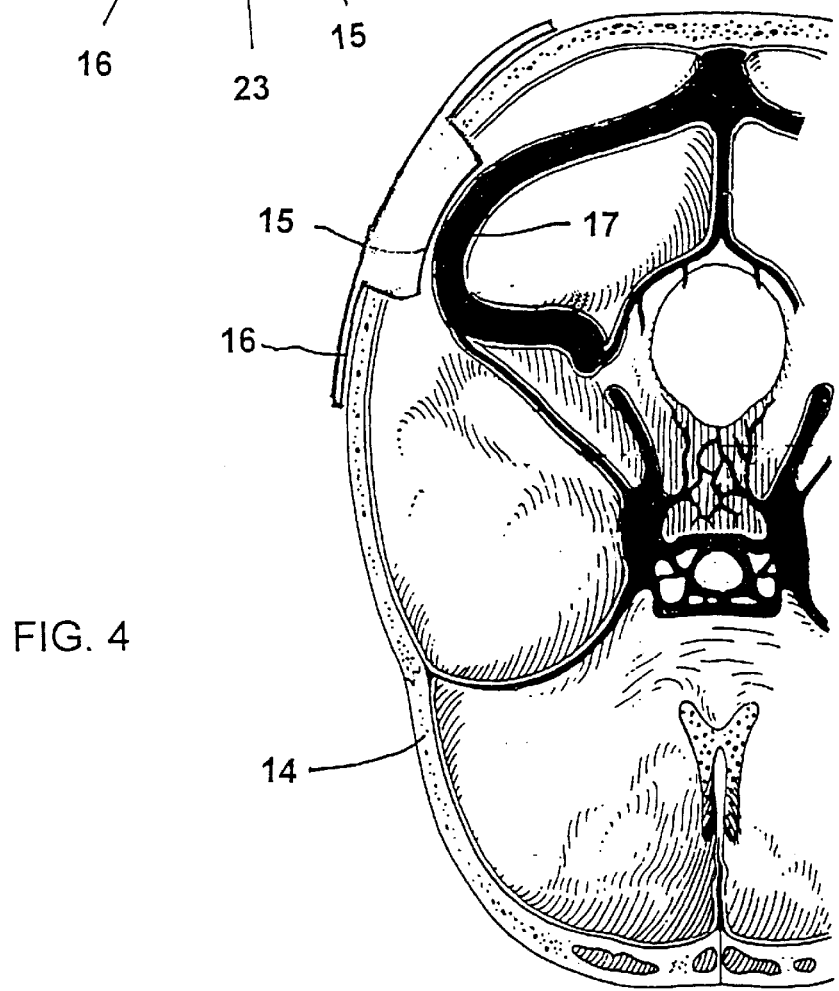
FIG. 4 shows an enlarged partial cross-sectional view as viewed from line IV—IV of FIG. 2.

As illustrated in FIGS. 1 to 4, a Seebeck effect-based thermoelectric energy converter 10 in accordance with one embodiment of the present invention may be implanted directly under the skin in the mastoid area 11 of the head 12 of a patient, i.e, between the skin 13 of the patient's head and the skull 14. The thermoelectric energy converter 10 has a hot pole 15 and a cold pole 16. In the illustrated embodiment, the hot pole 15 is positioned proximate to the sigmoid sinus 17 of the implant wearer as shown in FIG. 4 to provide a thermal coupling between the sigmoid sinus 17 and the hot pole 15. In contrast, the cold pole 16 of the thermoelectric energy converter 10 is positioned in the mastoid region 11 behind the ear and near the surface of the body so as to provide a thermal coupling between the surface of the body and the cold pole 16.

This positioning of the thermoelectric energy converter 10 provides special advantages in that the skull or neck areas of the implant wearer is hardly ever covered by heat-insulating clothing. Therefore, these areas normally have a temperature which is below the core temperature of the body. At the same time, the large blood vessels such as veins or arteries located in this area can provide a continuous heat energy supply which can permanently deliver sufficient thermal body energy as heat is continually converted into electric power by the thermoelectric energy converter 10 in accordance with the present invention. For example, the external jugular vein, the anterior jugular vein, the transverse sinus, or the external carotid artery, are all blood vessels in this area of the body which can serve as a heat energy supply. By applying the thermoelectric energy converter 10 of the present invention in these body areas in particular, a significant and continual temperature difference may be maintained to allow practical use and efficient powering of an active implant 26 such as a hearing device or other devices. Thus, a $\Delta T$ which is constant on average over time can be assumed so that electric power can be directly obtained by the Seebeck element without time limitation, stably over long durations, and without wear. In this regard, the application of the present invention in the mastoid region 11 as shown in FIGS. 1 to 4 is especially advantageous since there is sufficient bone structure available directly underneath the surface of the skin and the bony structure which covers the sigmoid sinus 17 is relatively easily accessible after a standard surgical procedure such as mastoidectomy. This ensures constant availability of thermal energy to the hot pole 15.

Figure 5:
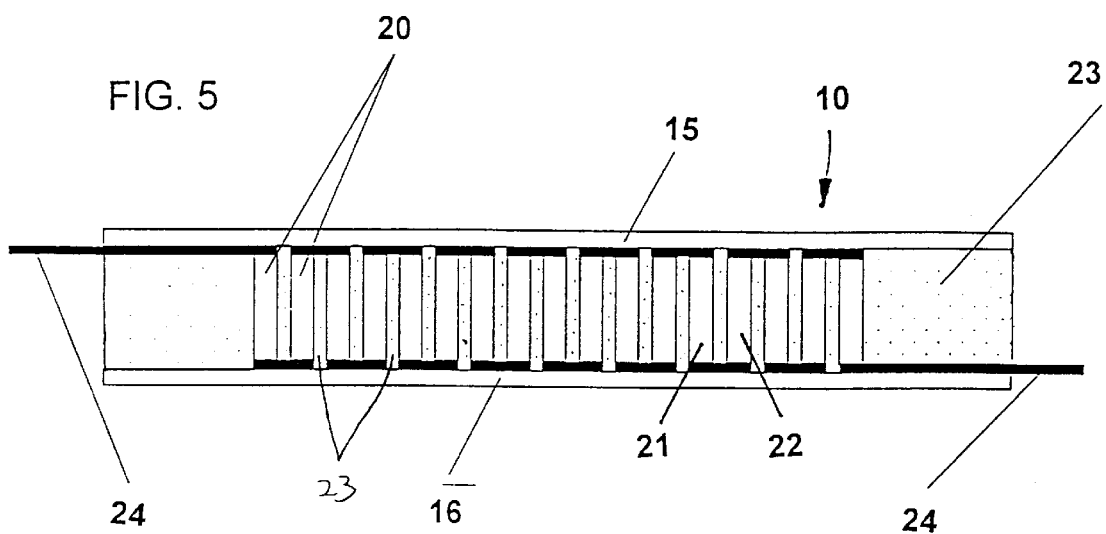
FIG. 5 shows an enlarged schematic side view of an energy converter in accordance with one embodiment of the present invention.
Figure 6:
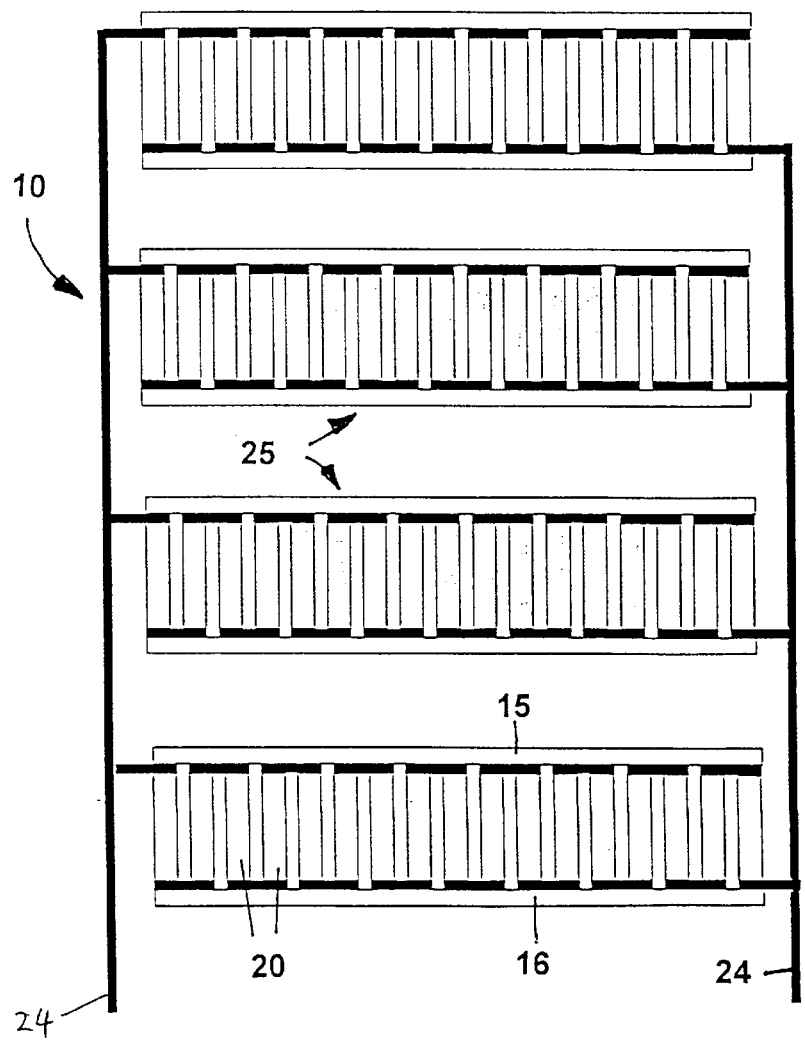
FIG. 6 is an enlarged schematic top view of an energy converter having numerous individual Seebeck modules electrically connected.

As shown in FIGS. 3, 5 and 6, the energy converter 10 in accordance with the illustrated embodiment may be provided with a plurality ("n"number) of electrically interconnected Seebeck elements or individual modules 20. Of course, the number of modules 20 may vary depending on the electrical power desired. As clearly shown in FIGS. 5 and 6, each individual module 20 may have two legs 21, 22 of materials having different electrical conductivity. One end of the legs 21, 22 is connected to the cold pole 16 and the other end is connected to the hot pole 15 of the thermoelectric energy converter 10 to allow transference of thermal energy. The individual modules 20 are mechanically interconnected by a thermally insulating composite element 23 located between the cold pole 16 and the hot pole 15. Because it is envisioned that the present invention be implanted in a patient, it is preferable that the composite element 23 be made of a biocompatible material. The structure of the thermoelectric energy converter 10 and its production process can include known features processes, such as those know from U.S. Pat. Nos. 4,095,998; 5,439, 528; and 5,430,322, Japanese patent publication 09 092 889 A European Patent No. 0 731 513, published PCT applications WO94/16464, WO 96/15412 and WO 97/44993.

The legs 21, 22 of the individual modules 20 in accordance with the present invention can be made of semiconductor materials with n-doping or p-doping. Alternatively, the legs 21, 22 may also be made of different metals which are spaced far apart in thermoelectric series. In this regard, material combinations for the semiconductor materials may be germanium-silicon mixed crystals and bismuth-tellurium combinations with suitably chosen doping. Additional fundamentally suitable material combinations are also described in published PCT application Nos. WO 94/14200. WO 95/04377 and in U.S. Pat. Nos. 5,747,728 and 5,356, 485, and the bibliographic citations listed there. The different metals which may be effectively used include especially pure titanium, titanium alloys, niobium, niobium alloys, tantalum, tantalum alloys, high quality steels and ceramics such as aluminum oxide ceramic.

It has been found in basic laboratory experiments with commercial Seebeck elements (individual modules) that:

At an assumed temperature difference of 0.5 degrees K, a cross sectional area of roughly 0.25 mm$^2$ and a volume of one element less than 1 mm$^3$, an electrical output power of roughly 0.5 $\mu$W can be achieved.

With only ten of these Seebeck elements, the continuous electrical output is roughly 5 $\mu$W. This output is sufficient to cover the stand-by power consumption of a modem cardiac pacemaker or neurostimulator as long as no neurostimulating impulse is delivered.

By a suitable arrangement of a large number (in the range above 100,000) of miniaturized Seebeck elements by processes of microsystem engineering or semiconductor lithography, for example, with suitable wiring of the individual elements, an overall system can be built which can continuously deliver electrical outputs in the range from 1 to 3 mW at a terminal voltage of 1 to 2 volts with an estimatable module surface in the range from 100 to 300 cm$^2$ and a temperature difference of 0.5 K. The electrical source impedance (internal resistance) is thus in the range from 100 to 300 ohms so that continuously operating implants such as hearing devices can be supplied with power.

FIG. 3 shows the thermally insulating composite element 23 as a separating layer between the hot pole 15 and the cold pole 16. In the embodiment shown in FIG. 5, the thermally insulating composite element 23 may be a casting material which fills the intermediate spaces between the individual modules 20, the cold pole 16, and the hot pole 15. The material of the thermally insulating composite element may be selected from the group consisting of polytetrafluorethylene, polycarbonates, polyurethane, silicones, and carbon fiber-reinforced polymers. The hermetic gas tightness which is otherwise required in such active implants that contain microelectronics is not absolutely necessary in this application, especially if small volumetric portions of water vapor do not damage the individual modules 20 internally over the long term and if the material does not introduce toxic substances into the body. The casting material of the thermally insulating composite element 23 may be silicone which is also easily compatible with the body. Moreover, as can be seen, the individual modules 20 are connected to other modules in series and electrical terminals 24 may also be provided to allow the electrical power generated by the thermoelectric energy converter 10 to be used in the manner discussed in further detail below.

In the embodiment of the present invention shown in FIG. 6, the thermoelectric energy converter 10 has a plurality of module groups 25 which are electrically connected to one another in parallel connection. As can also be seen, each module group 25 includes a plurality of individual modules 20 electrically connected to one another in a series. In another embodiment of the invention, the thermoelectric energy converter may include a plurality of module groups 25 of individual modules 20 electrically connected in series to one another, these module groups for their part being electrically connected in parallel. By a suitable arrangement of a large number (in the range exceeding 100,000) of miniaturized individual modules 20 (Seebeck elements), for example by processes of microsystem engineering or semiconductor lithography, an overall system can be built by corresponding electrical series-parallel connection and combining of individual elements into module groups, and can continuously deliver electrical outputs in the range from 1 to 3 mW at a terminal voltage of 1 to 2 volts for an estimatable module area in the range from 100 to 300 cm$^2$ and a temperature difference of 0.5 K. The electrical source impedance (internal resistance) can be in a range from 100 to 300 ohms so that a continuously operating sensory implant, such as hearing devices, can be supplied with power.

In particular, with reference to FIG. 4, the cold pole 16 in accordance with one embodiment of the present invention, can be advantageously formed as or coupled to a cooling body with an enlarged surface area in the manner shown which can be implanted directly under a skin surface of the implant wearer so as to maximize efficiency in conducting heat. Of course, the thermoelectric energy converter 10 can assume fundamentally any geometrical shape. It can it be built to be flat and smooth mainly using relatively small modules. In larger modules as especially applied in the implant wearer's head region and the mastoid area, an arched thermoelectric energy converter can be preferred which may be implemented to be only a few mm thick and shaped in a dome to optimally correspond to the arched surface of the skull.

Figure 7:
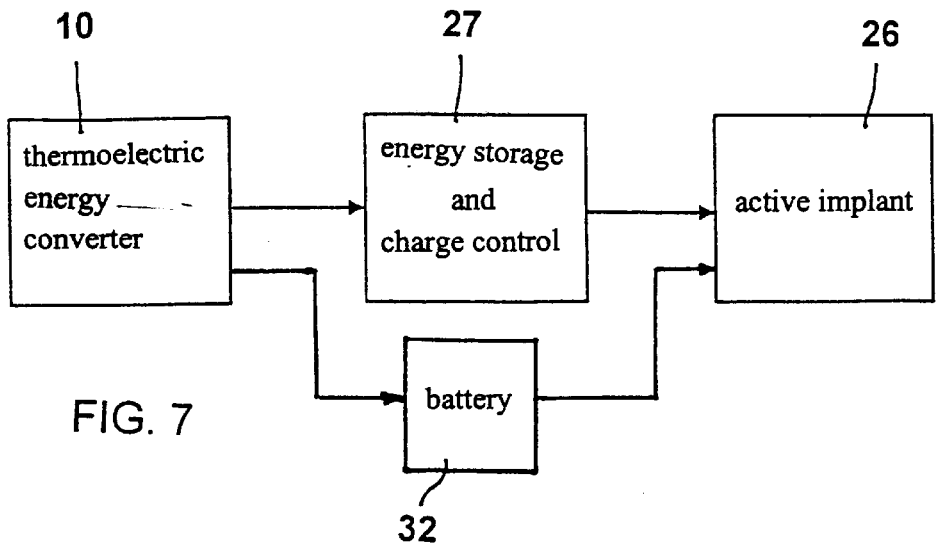
FIG. 7 is a block diagram for one application of the energy converter in accordance with the present invention.
Figure 8:
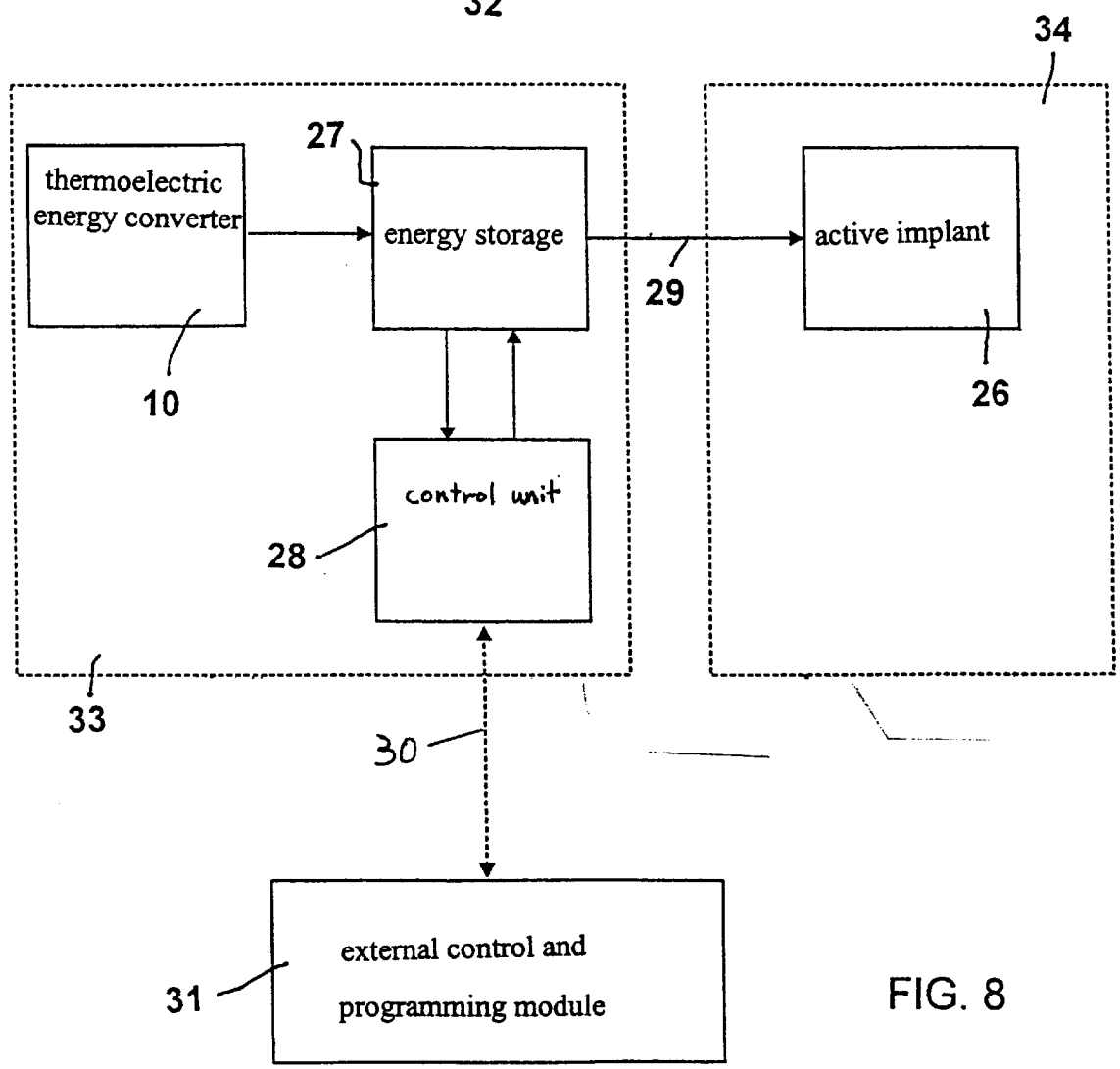
FIG. 8 is a block diagram for another application of the energy converter in accordance with the present invention.
Figure 9:
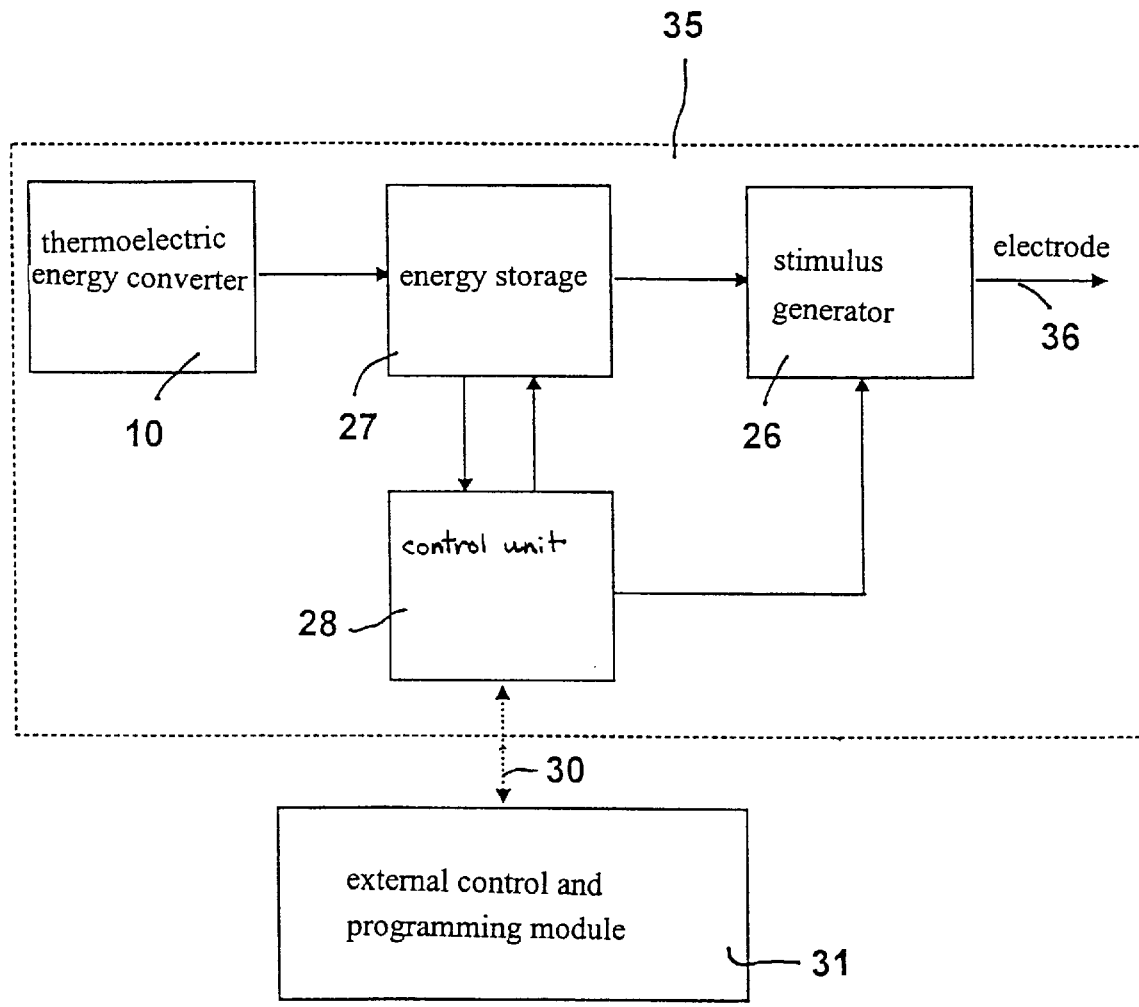
FIG. 9 is a block diagram for yet another application of the energy converter in accordance with the invention.

The application of the thermoelectric energy converter 10 in accordance with the present invention is illustrated in FIGS. 7 to 9. In the application illustrated in FIG. 7, the thermoelectric energy converter 10 provides the generated electrical power to the active implant 26 which may be a partially or filly implanted active device. Between the thermoelectric energy converter 10 and the active implant 26, an energy storage 27 device may be provided which may include long-lived capacitors (not shown) and a conventional energy management system. The electric power produced by the thermoelectric energy converter 10 can be collected and temporarily stored in an implantable energy storage 27 having a charge control until it is needed by the at least partially implanted active device such as the active implant 26. One typical application of the present invention is "on-demand"cardiac pacemakers which usually work in the "stand-by-mode" requiring only a few $\mu$W in this mode and providing a short, high energy stimulation impulse in the mW range for cardiac stimulation when necessary. Also, other neurostimulators which require higher operating energy for short stimulation pulses can be supplied in this way. For electrical storage 27 provided accordingly which may be long-lived capacitors (gold—Cap, OSCON—capacitors or high quality solid electrolyte—tantalum—capacitors) and having a charge control, a short-lived output demand peak for neurostimulation in the output range of a few mW can be delivered when these stimulation pulses take place at larger time intervals. Optionally, there can also be provided an implantable electrochemical secondary element such as a battery 32 which may be charged by the thermoelectric energy converter 10 either directly, or via the energy storage 27 when the electric power generated by the thermoelectric energy converter 10 is not needed by the active implant 26. Such battery 32 can be charged to distribute energy upon demand.

FIG. 8 illustrates another embodiment including an implantable control unit 28 designed to control the temporary storage of the electric power generated by the thermoelectric energy converter 10 in the implanted energy storage 27 and/or to regulate relay of electric power to the active implant 26 via electrical connection 29. The temporary storage of the electric power produced by the thermoelectric energy converter 10 in the energy storage 27 and/or power relay to the active implant 26 may be controlled by an implantable control unit 28 which may include a microprocessor or microcontroller (not shown) to which the corresponding peripheral hardware such as AD and DA converter, current actuators and the like (not shown). These peripheral hardware requires only very little electrical operating power since generally high-speed processes need not be handled. In the illustrated embodiment, the control unit 28 can be controlled and/or programmed by means of an external control and programming module 31 through a transcutaneous data link 30 from outside the body of the implant wearer. Thus, the implantable control unit 28 can be programmable wirelessly through the transcutaneous data link from outside the body of the implant wearer via a corresponding external control and programming module 31 in order to match the entire "programmable thermoelectric energy converter" system to the active implant 26 selected in the special application, whether it be a hearing device, a cardiac pacemaker, or some other at least partially implanted active implant. In the particular embodiment as shown in FIG. 8, the energy converter 10, the energy storage 27 and the control unit 28 may be combined into a first implant 33 while the active implant 26 may be a separate second implant 34 which is connected to the first implant 33 via the electrical connection 29.

FIG. 9 illustrates yet another embodiment in which the thermoelectric energy converter 10, the energy storage 27, the control unit 28 and the active implant 26, such as a stimulus generator are integrated in a single implant 35. In this embodiment, the active implant 26 such as the stimulus generator as well as the energy storage 27 and the control unit can be controlled and/or programmed by means of an external control and programming module 31 through a transcutaneous data link 30 from outside the body of the implant wearer. In this embodiment, the active implant 26 may be a stimulus generator which correspondingly, can generate an output 36 through a corresponding stimulation electrode. Thus, the thermoelectric energy converter 20 described here, can form a unit with the active implant 26 and correspondingly represent a single implant 35 ready for implantation. Here, in particular, active electronic hearing implants (not shown) should be mentioned which stimulate the inner ear with direct electrical stimulation such as a completely implantable cochlea implant or brain stem implant (see, for example, European Patent Nos. 0 076 070 and 0 124 930) or those which rehabilitate partial inner ear impairment such as sensorineural hearing losses with mechanical stimulation of the middle ear or inner ear. Systems of the latter type are known, among others, from U.S. Pat. Nos. 5,411,467 and 5,277,694.

Of course, these are only illustrative of applications of the present invention and the invention is not limited thereto. Moreover, the thermoelectric energy converter 10 can also be made as an independent implant, from which the electrical power may be delivered to the active implant 26 through a suitable, twin-pole plug-in connection and adequate electrical feed line. Thus, the thermoelectric energy converter 10 and the active implant 26 need not necessarily be positioned at the same implant site. For example, the thermoelectric energy converter 10 may be implanted in the mastoid while the active implant 26 (whether it be a cardiac pacemaker, other neurostimulator or other implant) is implanted elsewhere in the chest space, abdominal area or another location in the body and the electrical power is provided through an electric feed line through the neck.

While various embodiments in accordance with the present invention have been shown and described, it is understood that the invention is not limited thereto. These embodiments may be changed, modified and further applied by those skilled in the art. Therefore, this invention is not limited to the details shown and described previously but also includes all such changes and modifications which are encompassed by the appended claims.

We claim:

1. Process for supplying electric power generated by an implanted thermoelectric power converter to an at least partially implanted active device comprising the steps of:
    positioning a hot pole of said thermoelectric power converter in an area of an implant wearer's body in a manner that said hot pole is maintained at substantially the core temperature of the wearer's body; and
    positioning a cold pole of said thermoelectric power converter in an area of a implant wearer's body proximal to an outer skin surface in a manner that said cold pole is maintained at a substantially outer skin temperature of the wearer's body.

2. Process of claim 1, further comprising the step of collecting and temporarily storing electric power generated by the energy converter in an implanted energy storage until the electric power is needed by said at least partially implanted active device.

3. Process for supplying electric power generated by an implanted thermoelectric power converter to an at least partially implanted active device comprising the steps of:
    positioning a hot pole of said thermoelectric power converter in at least one of an implant wearer's skull and the implant wearer's neck in a manner that said hot pole is maintained at substantially at the core temperature of the wearer's body; and
    positioning a cold pole of said thermoelectric power converter in an area of a implant wearer's body proximal to an outer skin surface of at least one of the implant wearer's skull and the implant wearer's neck in a manner that said cold pole is maintained at a substantially outer skin temperature of the wearer's body.

4. Process of claim 3, further comprising the step of positioning said hot pole proximate to a large blood vessel in a manner to transfer heat from the large blood vessel to the hot pole.

5. Process of claim 4, further comprising the step of positioning said hot pole proximate to the implant wearer's sigmoid sinus and positioning said cold pole in the implant wearer's mastoid region proximate to the outer skin of said region.

6. Process of claim 3, further comprising the step of collecting and temporarily storing electric power generated by the energy converter in an implanted energy storage until the electric power is needed by said at least partially implanted active device.

7. Process of claim 6, further comprising the step of controlling the collection and temporary storage of electric power using an implantable control unit.

8. Process of claim 7, further comprising the step of programming said implantable control unit through one of an unidirectional and a bidirectional transcutaneous data link from outside of the implant wearer's body.

9. An implantable thermoelectric energy converter for converting thermal energy generated by an implant wearer into electrical power for supplying electric power to an at least partially implanted active device, said implantable thermoelectric energy converter comprising:
    a hot pole;
    a cold pole; and
    a plurality of individual modules which are electrically coupled to one another and are disposed between said hot pole and said cold pole;
    wherein said hot pole is adapted to thermally couple one end of said plurality of individual modules to an implantation site having a temperature substantially that of a core body temperature and said cold pole is adapted to thermally couple another end of said plurality of individual modules to an implantation site which is closer to an outer skin surface of the implant wearer when said thermoelectric energy converter is implanted.

10. An implantable thermoelectric energy converter of claim 9, further comprising an implantable energy storage for collecting and temporarily storing electric power generated.

11. An implantable thermoelectric energy converter of claim 9, wherein said cold pole forms a cooling body having an enlarged surface area, said cooling body being adapted to be positioned directly under a skin surface of the implant wearer.

12. An implantable thermoelectric energy converter of claim 9, wherein said cold pole is thermally coupled to a cooling body having a large surface area, said cooling body being adapted to be positioned under a skin surface of the implant wearer.

13. An implantable thermoelectric energy converter for converting thermal energy generated by an implant wearer into electrical power for supplying electric power to an at least partially implanted active device, said implantable thermoelectric energy converter comprising:

a hot pole;

a cold pole; and a plurality of individual modules which are electrically coupled to one another and are disposed between said hot pole and said cold pole;

wherein said hot pole is adapted to thermally couple one end of said plurality of individual modules to an implantation site located in at least one of the implant wearer's skull and the implant wearer's neck having a temperature substantially that of a core body temperature and said cold pole is adapted to thermally couple another end of said plurality of individual modules to an implantation site in at least one of the implant wearer's skull and the implant wearer's neck closer to an outer body surface of the implant wearer.

14. An implantable thermoelectric energy converter of claim 13, wherein said hot pole is adapted to thermally couple one end of said plurality of individual modules to a blood vessel in at least one of the implant wearer's skull and the implant wearer's neck when said thermoelectric energy converter is implanted.

15. An implantable thermoelectric energy converter of claim 14, wherein said hot pole is adapted to thermally couple one end of said plurality of individual modules to a sigmoid sinus of the implant wearer and said cold pole is adapted to thermally couple another end of said plurality of individual modules closer to the outer body surface at a mastoid region of the implant wearer.

16. An implantable thermoelectric energy converter of claim 13, further comprising an implantable energy storage for collecting and temporarily storing electric power generated.

17. An implantable thermoelectric energy converter of claim 16, further comprising an implantable control unit for controlling at least one of said energy storage and relay of electrical power to said active implant.

18. An implantable thermoelectric energy converter of claim 17, wherein said implantable control unit includes at least one of a microprocessor and a microcontroller.

19. An implantable thermoelectric energy converter of claim 17, further comprising an external control and programming module for at least one of controlling and programming said implantable control unit through a transcutaneous data link from outside the implant wearer's body.

20. An implantable thermoelectric energy converter of claim 13, wherein each of said plurality of individual module includes legs of different electrical conductivity, one end of each of said two legs being connected to said cold pole, and another end of each of said legs being connected to said hot pole.

21. An implantable thermoelectric energy converter of claim 20, wherein said legs comprises at least one of an n-doped semiconductor material and a p-doped semiconductor material.

22. An implantable thermoelectric energy converter of claim 20, wherein said legs have different metals which are spaced far apart in thermoelectric series.

23. An implantable thermoelectric energy converter of claim 13, wherein said cold pole and said hot pole are formed of a biocompatible material having thermally conductive property.

24. An implantable thermoelectric energy converter of claim 23, wherein said biocompatible material is selected from a group consisting of titanium, titanium alloys, niobium, niobium alloys, tantalum, tantalum alloys, steels and aluminum oxide ceramic.

25. An implantable thermoelectric energy converter of claim 13, wherein said plurality of individual modules are mechanically interconnected by a thermally insulating composite element made of a biocompatible material, said thermally insulating composite element being located between said cold pole and said hot pole.

26. An implantable thermoelectric energy converter of claim 25, wherein said biocompatible material for said thermally insulating composite element is selected from a group consisting of polytetrafluorethylene, polycarbonates, polyurethane, silicones, and carbon fiber-reinforced polymers.

27. An implantable thermoelectric energy converter of claim 25, wherein said thermally insulating composite element fills intermediate spaces in the form of casting material between said plurality of individual modules, said cold pole and said hot pole.

28. An implantable thermoelectric energy converter of claim 13, further comprising a plurality of module groups, each of said plurality of module groups being electrically connected in parallel to one another and including a plurality of individual modules electrically connected in series to one another.

29. An implantable thermoelectric energy converter of claim 13, wherein said cold pole forms a cooling body adapted to be implanted directly under the implant wearer's skin.

30. An implantable thermoelectric energy converter of claim 13, wherein said cold pole is coupled to a cooling body having an enlarged surface area, said cooling body being adapted to be positioned directly under a skin surface of the implant wearer.

31. An implantable thermoelectric energy converter of claim 13, wherein said implantable thermoelectric energy converter is substantially planar in shape.

32. An implantable thermoelectric energy converter of claim 31, wherein said implantable thermoelectric energy converter is substantially arched in shape to generally correspond to an arched shape of a human skull.

* * * * *